United States Patent
Ternes et al.

(10) Patent No.: US 9,757,569 B2
(45) Date of Patent: Sep. 12, 2017

(54) SENSING WINDOW MANAGEMENT OF MULTIPOINT PACING

(71) Applicant: Cardiac Pacemakers, Inc., St. Paul, MN (US)

(72) Inventors: David J. Ternes, Roseville, MN (US); William J. Linder, Golden Valley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 15/013,243

(22) Filed: Feb. 2, 2016

(65) Prior Publication Data
US 2016/0228709 A1 Aug. 11, 2016

Related U.S. Application Data

(60) Provisional application No. 62/112,192, filed on Feb. 5, 2015.

(51) Int. Cl.
*A61N 1/368* (2006.01)
*A61N 1/05* (2006.01)
*A61N 1/365* (2006.01)

(52) U.S. Cl.
CPC .......... *A61N 1/3686* (2013.01); *A61N 1/056* (2013.01); *A61N 1/3682* (2013.01); *A61N 1/3684* (2013.01); *A61N 1/36514* (2013.01)

(58) Field of Classification Search
CPC .. A61N 1/3686; A61N 1/056; A61N 1/36514; A61N 1/3682; A61N 1/3684
See application file for complete search history.

(56) References Cited

U.S. PATENT DOCUMENTS 8,612,000 B2* 12/2013 Stahmann ............ A61N 1/3627
607/17
2004/0243190 A1* 12/2004 Ben-Haim ........... A61B 5/0215
607/9

(Continued)

FOREIGN PATENT DOCUMENTS

| EP | 1529551 A1 | 5/2005 |
|---|---|---|
| WO | WO-2016126654 A2 | 8/2016 |
| WO | WO-2016126654 A3 | 8/2016 |

OTHER PUBLICATIONS

"International Application Serial No. PCT/US2016/016086, International Search Report mailed Aug. 23, 2016", 9 pgs.

(Continued)

*Primary Examiner* — Catherine Voorhees
(74) *Attorney, Agent, or Firm* — Schwegman Lundberg & Woessner, P.A.

(57) ABSTRACT

An apparatus for coupling to a plurality of electrodes implantable at a plurality of tissue sites of a heart chamber of a subject. The apparatus including a stimulus circuit configured to provide an electrical cardiac pacing stimulation to the plurality of electrodes, a switching circuit configured to select electrodes of the plurality of electrodes for electrical coupling to the stimulus circuit, and a control circuit including a heart rate sub-circuit configured to determine heart rate; and a pacing site activation sub-circuit configured to selectively change which electrodes of the plurality of electrodes are used to provide the electrical cardiac pacing stimulation therapy according to the determined heart rate.

20 Claims, 5 Drawing Sheets

(56) References Cited

U.S. PATENT DOCUMENTS

| | | | |
|---|---|---|---|
| 2009/0234413 A1* | 9/2009 | Sambelashvili | A61N 1/3627 607/25 |
| 2013/0030314 A1* | 1/2013 | Keel | A61B 5/0422 600/518 |
| 2013/0131750 A1 | 5/2013 | Stadler et al. | |
| 2014/0067002 A1 | 3/2014 | Arcot-krishnamurthy et al. | |
| 2014/0188184 A1 | 7/2014 | Maskara et al. | |
| 2016/0114169 A1* | 4/2016 | Sheldon | A61N 1/3704 607/17 |

OTHER PUBLICATIONS

"International Application Serial No. PCT/US2016/016086, Invitation to Pay Additional Fees and Partial Search Report mailed Jun. 27, 2016", 8 pgs.

"International Application Serial No. PCT/US2016/016086, Written Opinion mailed Aug. 23, 2016", 8 pgs.

\* cited by examiner

SENSING WINDOW MANAGEMENT OF MULTIPOINT PACING

CLAIM OF PRIORITY

This application claims the benefit of priority under 35 U.S.C. §119(e) of U.S. Provisional Patent Application Ser. No. 62/112,192, filed on Feb. 5, 2015, which is herein incorporated by reference in its entirety.

BACKGROUND

Ambulatory medical devices include implantable medical devices (IMDs) and wearable medical devices. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of IMDs include implantable diagnostic devices, implantable drug delivery systems, or implantable devices with neural stimulation capability (e.g., vagus nerve stimulator, baroreflex stimulator, carotid sinus stimulator, etc.).

Some examples of wearable medical devices include wearable cardioverter defibrillators (WCDs) and wearable diagnostic devices (e.g., an ambulatory monitoring vest). WCDs can be monitoring devices that include surface electrodes. The surface electrodes may be arranged to provide one or both of monitoring to provide surface electrocardiograms (ECGs) and delivery of cardioverter and defibrillator shock therapy. A wearable medical device can also include a monitoring patch worn by the patient such as an adherable patch or a patch included with an article of clothing worn by the patient.

Therapy provided by ambulatory medical devices is typically optimized by a caregiver, such as by programming different operating parameters of the medical device for example. Manufacturers of such devices continue to improve and add functionality to the devices, which can make them complicated to program and optimize to the needs of a particular patient. The inventor has recognized a need for improved optimization of device-based therapy.

OVERVIEW

As explained above, manufacturers of CRM devices continue to improve and add functionality to the devices, which may result in complex interactive limits on programmable device parameter settings. The present subject matter relates to providing multi-site pacing therapy in a manner that minimizes complexity of the resulting interactive parameter limits.

An apparatus example of the present subject matter includes a plurality of electrodes implantable at a plurality of tissue sites of a heart chamber of a subject, a stimulus circuit configured to provide an electrical cardiac pacing stimulation to the plurality of electrodes, a switching circuit configured to select electrodes of the plurality of electrodes for electrical coupling to the stimulus circuit, and a control circuit including a heart rate sub-circuit configured to determine heart rate; and a pacing site activation sub-circuit configured to selectively change which electrodes of the plurality of electrodes are used to provide the electrical cardiac pacing stimulation therapy according to the determined heart rate.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
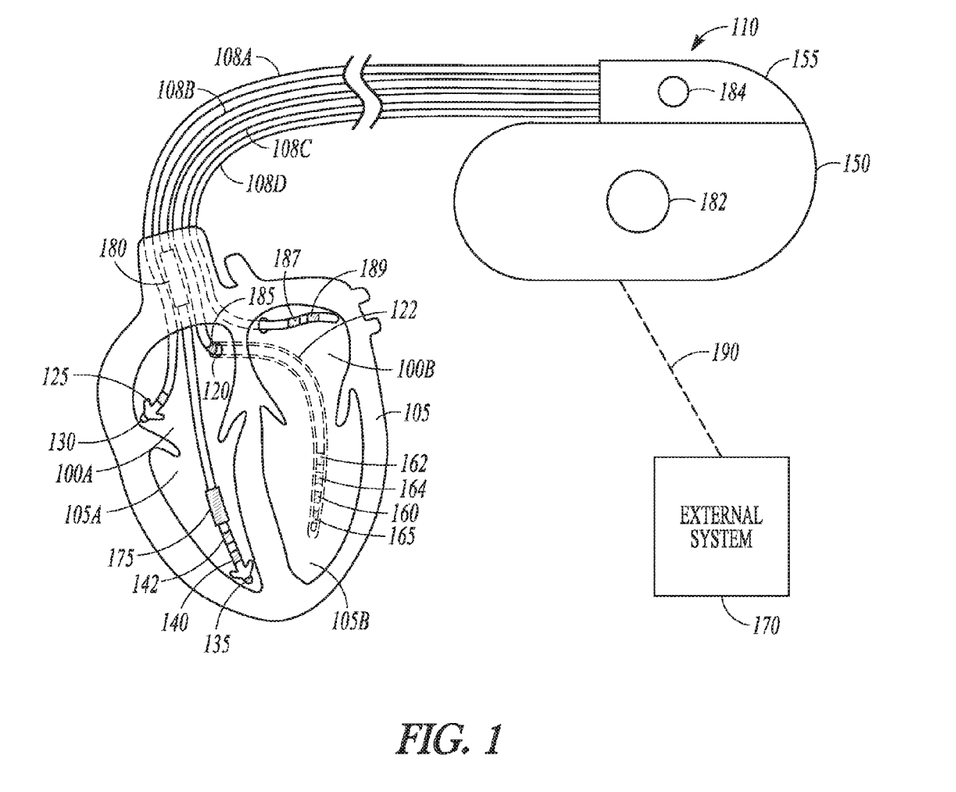
FIG. 1 is an illustration of an example of portions of a system that includes an IMD.

FIG. 1 is an illustration of portions of a system that includes an IMD 110. Examples of IMD 110 include, without limitation, a pacemaker, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. RV lead 108B can include one or more additional ring electrodes 142 to provide multi-site pacing the RV. Lead 108B optionally also includes additional electrodes, such as electrodes 175 and 180, for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes electrodes 160, 162, 164, and 165 placed in a coronary vein 122 lying epicardially on the left ventricle (LV) 105B via the coronary vein. The number of electrodes shown in the Figure is only an example and other arrangements are possible. For instance, the third cardiac lead 108C may include less electrodes (e.g., one or two electrodes) or more electrodes (e.g., eight or more electrodes) than the example shown, and may include a ring electrode 185 positioned near the coronary sinus (CS) 120.

In addition to cardiac leads 108A, 108B, 108C, or in alternative to one or more of cardiac leads 108A, 108B, 108C, the IMD 110 can include a fourth cardiac lead 108D that includes electrodes 187 and 189 placed in a vessel lying epicardially on the left atrium (LA) 100B.

The IMD 110 can include a hermetically-sealed IMD housing or can 150, and the IMD 110 can include an electrode 182 formed on the IMD can 150. The IMD header 155 may also include an electrode 184. Cardiac pacing therapy can be delivered in a unipolar mode using the electrode 182 or electrode 184 and one or more electrodes formed on a lead. Cardiac pacing therapy can be delivered in an extended bipolar pacing mode using only one electrode of a lead (e.g., only one electrode of LV lead 108C) and one electrode of a different lead (e.g., only one electrode of RV lead 108B). Cardiac pacing therapy can be delivered in a monopolar pacing mode using only one electrode of a lead without a second electrode.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to the electrode 182 formed on the IMD can 150. This improves defibrillation by delivering current from the RV coil 175 more uniformly over the ventricular myocardium. In some examples, the therapy is delivered from the RV coil 175 only to the electrode 182 formed on the IMD can 150. In some examples, the coil electrodes 175, 180 are used in combination with other electrodes for sensing signals.

Note that the specific arrangement of leads and electrodes are shown the illustrated example of FIG. 1 is intended to be non-limiting. An IMD can be configured with a variety of electrode arrangements including transvenous, endocardial, and epicardial electrodes (e.g., an epicardial patch that may include dozens of electrodes), and/or subcutaneous, non-intrathoracic electrodes. Any of the implantable leads described may include more than the number of leads shown. An IMD 110 can be connectable to subcutaneous array or lead electrodes (e.g., non-intrathoracic electrodes or additional LV leads implantable along the LV wall, and leads implantable in one or both atria) that can be implanted in other areas of the body to help "steer" electrical currents produced by IMD 110.

An IMD can be leadless (e.g., a leadless pacemaker). A leadless IMD may be placed in a heart chamber (e.g., RV or LV) and multiple electrodes of the leadless IMD may contact cardiac tissue. The present methods and systems will work in a variety of configurations and with a variety of electrodes.

As explained previously, functionality of ambulatory medical devices can make them complicated for a caregiver to program and optimize to the needs of a particular patient. For instance, a CRM device may provide multi-site pacing, in which pacing pulses are provided to multiple sites within a same heart chamber. This may be useful to improve coordination of a contraction of a heart chamber, especially of the left ventricle. In the non-limiting example shown in FIG. 1, pacing may be provided to left ventricular electrodes 160, 162, 164, 165 in a specified sequence to coordinate activation at different tissue sites of the left ventricle to a cause a left ventricular (LV) contraction in a desired fashion. As an illustrative example, there may be a time delay between activation of right ventricular (RV) ring electrode 140 and LV tip electrode 165 (LV1). There may be additional time delays between the LV1 and LV electrode 160 (LV2), between LV2 and LV electrode 164 (LV3), and between LV3 and LV electrode 162 (LV4). The time delays may be the same or may be individually programmable. Electrode activation may take place in a different order than from LV1 to LV4. There can also be a programmable time delay between an intrinsic atrial event and a pace in a ventricle (intrinsic AV delay).

Electrodes are also used to sense intrinsic electrical cardiac activity such as intrinsic depolarization to trigger electrical pacing therapy and to sense cardiac tachyarrhythmia which may trigger delivery of anti-tachyarrhythmia therapy.

Sensing time windows for cardiac activity detection are enabled in a specified relation to paced events to avoid misidentifying a paced cardiac depolarization as intrinsic activity. The sensing time windows may be enabled after one or both of a blanking period and a refractory period after pacing stimulation is delivered.

The multi-site pacing may have an impact on these detection windows. For instance, a caregiver may program a CRM device to have a resting heart rate of sixty beats per minute (60 bpm), corresponding to a maximum rate interval of 1000 milliseconds (ms). The caregiver may also program an atrial-ventricular (AV) delay of 200 ms, a right ventricular to left ventricular delay (e.g., RV-LV1) of 50 ms, with intra-ventricular pacing delays of 10 ms (e.g., LV1-LV2=LV2-LV3=LV3-LV4=10 ms). This results in a total delay of 280 ms. The caregiver may also program a refractory period of 135 ms for a total of 415 ms. This leaves 1000 ms-415 ms=585 ms for a sensing time window. If rate responsive pacing is also enabled, the pacing interval may decrease as the pacing rate is increased in response to patient physical activity (e.g., exercise). If the pacing rate is increased to 120 bpm (pacing interval of 500 ms), the time available for a sensing time window becomes small (500 ms-415 ms=85 ms) and intrinsic cardiac activity may be undetected.

Figure 2:
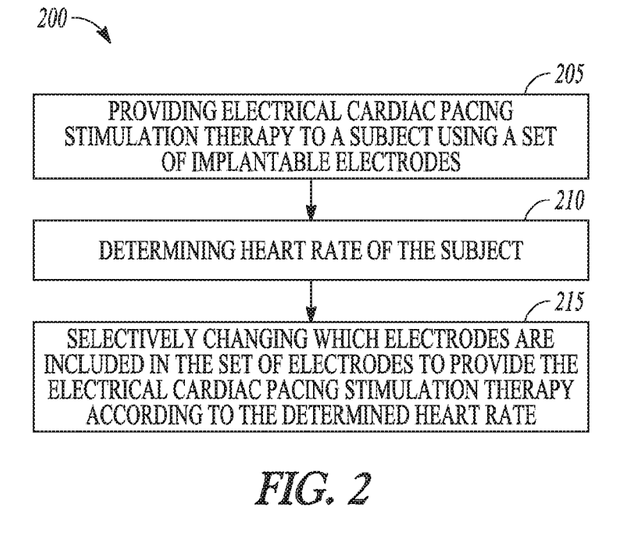
FIG. 2 shows a flow diagram of an example of a method of operating an implantable or otherwise ambulatory medical device.

FIG. 2 shows a flow diagram of an example of a method 200 of operating an implantable or otherwise ambulatory medical device. At 205, electrical cardiac pacing stimulation therapy is provided to a subject using a set of a plurality of implantable electrodes. In some examples, pacing stimulation therapy is provided to multiple sites within the left ventricle of the subject.

At 210 heart rate of the subject is determined. The heart rate may be a measured intrinsic heart rate, or the heart rate may be an activity-based pacing rate calculated or otherwise determined by the medical device.

At 215, the electrodes that are included in the set of electrodes to provide the electrical cardiac pacing stimulation therapy is selectively changed according to the determined heart rate. When the heart rate increases (e.g., to a first specified heart rate threshold), one or more of the electrodes can be removed from the set used to deliver therapy. When the heart rate decreases (e.g., below the threshold), electrodes can be replaced in the set used to deliver therapy.

In the example described previous, if the pacing rate is increased to 120 bpm (pacing interval of 500 ms), the time available for a sensing time window became quite small (500 ms-415 ms=85 ms). If all but the LV1 pacing site is dropped at the higher rate, the total delay is reduced to 250 ms. If the refractory period is not changed, the time available for a sensing detection window is increased to 115 ms (500 ms-385 ms=115 ms). This provides a larger time window in which intrinsic activity may be sensed.

If the time delays are dynamic, more time can be made available for sensing. For instance, the AV delay may be reduced with the increase in heart rate. If the AV delay is reduced to 100 ms at a pacing interval of 500 ms, the time available for a sensing time window is increased to 115 ms (500 ms-285 ms=215 ms). Inter-ventricular delay (e.g., RV-LV1 delay) can also be reduced with the increase in rate. If the RV-LV1 delay is reduced from 50 ms to 20 ms at a pacing interval of 500 ms, the time available for a sensing time window is increased to 245 ms (500 ms-255 ms=245 ms). Intra-ventricular delays (e.g., LV1 -LV2 delay) can also be reduced with an increase in heart rate. The intra-ventricular electrodes remaining in use can be educed (e.g., from 10 ms to 5 ms) to increase time available for a sensing time window.

Figure 3:
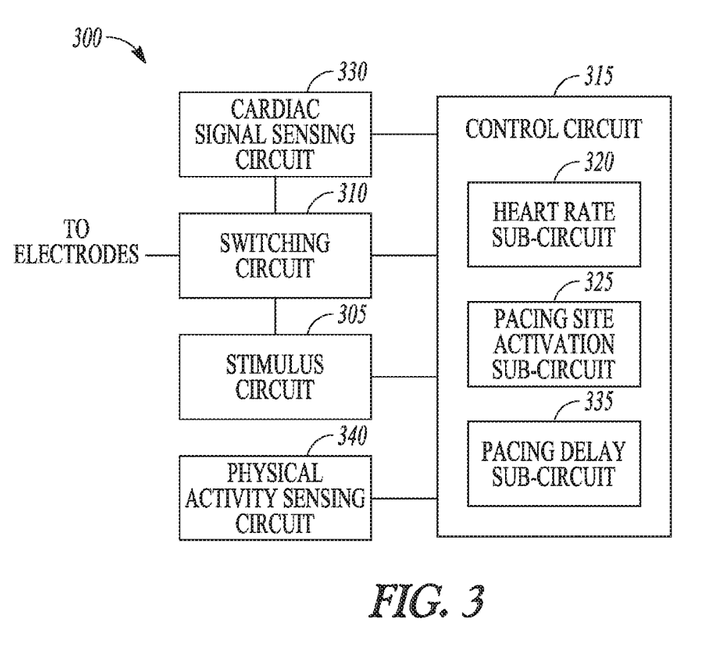
FIG. 3 shows a block diagram of portions of an example of an implantable or otherwise ambulatory medical device.

FIG. 3 shows a block diagram of portions of an example of an implantable or otherwise ambulatory medical device. The device 300 includes a stimulus circuit 305 that provides electrical cardiac pacing stimulation to a plurality of electrodes. The electrodes are implantable at a plurality of tissue sites of one or both ventricles of a heart of a subject. Examples of such electrodes were described previously in regard to FIG. 1. The device 300 includes a switching circuit 310 that selects electrodes for electrical coupling to the stimulus circuit.

The device 300 also includes a control circuit 315. The control circuit 315 can include a microprocessor, a digital signal processor, application specific integrated circuit (ASIC), or other type of processor, interpreting or executing instructions included in software or firmware. The control circuit 315 can include other circuits and sub-circuits to perform the functions described. These circuits and sub-circuits may include software, hardware, firmware or any combination thereof. Multiple functions can be performed in one or more of the circuits and sub-circuits as desired.

The control circuit 315 includes a heart rate sub-circuit 320 that determines heart rate. The heart rate may be a sensed intrinsic rate or may be a pacing rate. For instance, the device 300 may include a physical activity sensing circuit 340 that generates an activity signal representative of physical activity of the subject. The heart rate sub-circuit 320 determines a paced heart rate according to the activity signal. The control circuit 315 also includes a pacing site activation sub-circuit 325 selectively changes which electrodes are used to provide the electrical cardiac pacing stimulation therapy according to a paced heart rate or a measured intrinsic heart rate.

In some embodiments, the device 300 includes a cardiac signal sensing circuit 330 that senses electrical cardiac activity signal via the electrodes. The control circuit 315 may use signals that are sensed during a sensing time window of a cardiac cycle to determine device behavior. In some variations, the control circuit 315 uses the sensed cardiac signals to detect intrinsic activity that affects pacing behavior. For example, sensed atrial activity may be used to time delivery of pacing stimulation to one or both ventricles, and sensed ventricular activity may be used to inhibit pacing or time a pacing stimulation provided to the other ventricle (e.g., cardiac resynchronizaton therapy). In some variations, the control circuit 315 uses the sensed cardiac signals to detect arrhythmia such as cardiac tachyarrhythmia and to initiate delivery of one or more of anti-tachycardia pacing therapy, cardioversion therapy, and defibrillation therapy. Based on the electrode change the control circuit 315 may be able to adjust the specified sensing time window.

If heart rate increases, the size of the sensing time window may decrease due to one or both of refractory and blanking periods, and this may result in intrinsic cardiac activity being undetected. Reducing the number of electrodes used to deliver the electrical pacing therapy can make more time available for the sensing time window at the higher heart rate. The electrodes that were removed from delivery of pacing therapy can be added back in to the therapy when the heart rate decreases. In some variations, the electrodes are added back in according to heart rate and in some variations the electrodes are added back according to the size of the sensing time window available.

In some examples, the electrodes include multiple electrodes implantable in the left ventricle (LV). The device 300 may include a pacing delay sub-circuit 335 that determines a time delay between delivery of a pacing stimulus pulse to a first electrode at a first pacing site of the LV and delivery of a pacing pulse to a second electrode at a second pacing site of the LV. For instance, the pacing delay sub-circuit 335 may determine a time delay between any of LV tip electrode 165, LV electrode 160, LV electrode 164, and LV electrode 162 in FIG. 1. The pacing site activation sub-circuit 325 may change which of the electrodes are used to provide pacing stimulus pulses to the left ventricle according to the determined heart rate.

Figure 4:
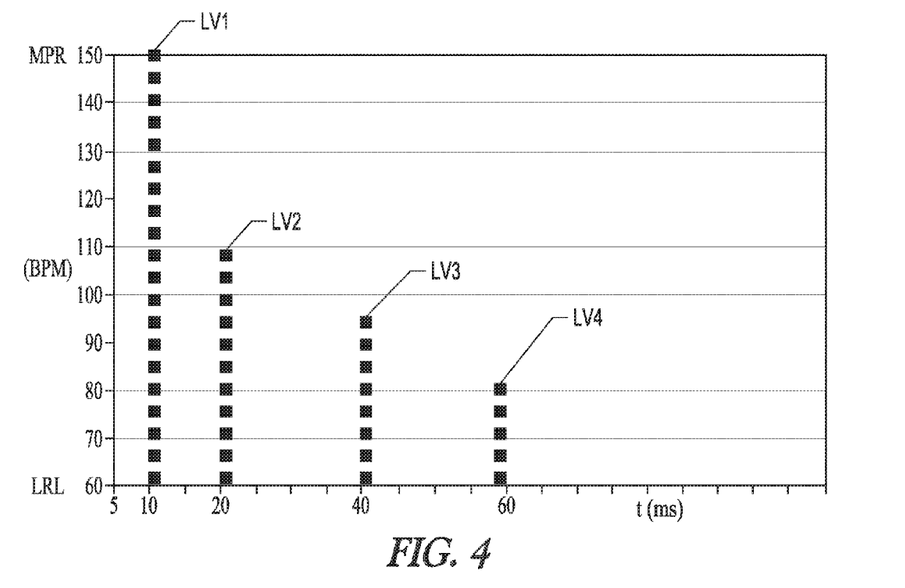
FIG. 4 is a graph that illustrates an example of a medical device automatically changing electrode activation according to heart rate.

FIG. 4 is a graph that illustrates an example of a medical device automatically changing electrode activation according to heart rate. The vertical or y-axis represents heart rate in bpm. Starting with a lower rate limit (LRL) of 60 bpm and extending up to a maximum pacing rate (MPR) of 150 bpm. The horizontal or x-axis represents activation times using electrodes arranged in the LV or in both the RV and LV. As an illustrative example intended to be non-limiting, the electrodes used to deliver the pacing stimuli to the left ventricle correspond to LV electrode 165 (LV1), LV electrode 160 (LV2), LV electrode 164 (LV3), and LV electrode 162 (LV4) in FIG. 1. In certain variations, there are more than four electrodes in the LV providing multi-site pacing therapy. The vertical bars represent activation times for the electrodes. The activation times may be relative to cardiac activity in the RV that is paced or intrinsic. At the LRL, four pacing stimuli are delivered to the LV at different times to coordinate an LV contraction. Electrode LV1 is activated at about 5 ms after the RV activity (RV-LV1 delay) and the vertical bar positioned at 10 ms represents activation for the LV1 electrode. The LV2 electrode is activated at about 20 ms (LV1-LV2 delay), the LV3 electrode is activated at about 40 ms (LV2-LV3 delay), and the LV4 electrode is activated at about 60 ms (LV3-LV4 delay), and the vertical bars at 20 ms, 40 ms and 60 ms positions represent activations for the LV2, LV3, and LV4 electrodes respectively. The pacing stimuli may delivered in a unipolar pacing mode (e.g., between each of LV1, LV2, LV3, LV4 and an electrode formed on the medical device can) or in a bipolar pacing mode. As the heart rate increases, the pacing site activation sub-circuit 325 drops electrodes from the pacing regimen.

The graph of FIG. 4 shows an example of the heart rate thresholds above the LRL at which pacing activation sites are dropped. From 60 bpm until 80 bpm, four pacing stimuli are delivered to the LV at about 10 ms, 20 ms, 40 ms and 60 ms. Above 80 bpm, the LV4 electrode is dropped from the pacing regimen. From 81 bpm until 95 bpm three pacing stimuli are delivered to the LV. Above 95 bpm, electrode LV3 is dropped. From 96 bpm until 110 bpm two pacing stimuli are delivered to the LV at about 10 ms and 20 ms. At heart rates above 111 bpm, electrode LV2 is dropped and one pacing stimuli is delivered at about 10 ms.

In some examples, as the heart rate decreases, the electrodes are activated at the same heart rate in which the electrode was removed. For instance, when the heart rate decreases from the MPR to 110 bpm, electrode LV2 is added back to the pacing regiment and two pacing stimuli are delivered to the LV at about 10 ms and 20 ms. In some examples, hysteresis is used when re-activating electrodes. To implement hysteresis, the pacing site activation sub-circuit 325 restores the electrode in the set of electrodes used to deliver the pacing stimulation therapy when the determined heart rate decreases to a second specified heart rate threshold lower than the first heart rate threshold. For instance, electrode LV2 may be added back to the pacing regimen when the heart decreases below 100 bpm.

In some examples, as the heart rate decreases, the electrodes are re-activated according to the sensing time window available. For instance, electrode LV3 may not be re-activated until a heart rate less than 95 bpm so that a specified sensing time window can be provided.

The order in which electrodes are dropped can be flexible. In some examples, the electrode corresponding to the latest pacing activation site is dropped first. The dropped pacing site may correspond to the latest time delay. In certain variations, the first electrode used in a series (e.g., LV1 in the example) is dropped first. In some examples, electrodes can be dropped according to the physical location of the electrode. In certain variations, the order that the electrodes are dropped is programmed by a user (e.g., a physician).

As explained previously, a sensing time window may be adjusted according to a determined heart rate that may be a sensed intrinsic rate or a calculated paced rate. Different electrode activations may be used for paced and sensed rates. For instance, it may be desired for one or both of a blanking period and refractory period to be longer for a paced event. This may lead to deactivation of more electrodes at a paved rate to make more time available for the sensing time window.

In certain examples, it may be desired to have a longer sense time window for a sensed intrinsic event versus a paced event to allow more time to detect intrinsic activity. Thus, electrode activation may be different for sensed atrial or ventricular events versus paced atrial or ventricular events. For similar reasons, electrode activation may be different for a ventricular heart rate that is tracking events in the atrium versus a heart rate that is sensor driven (e.g., driven by patient physical activity). In certain examples, the pacing site activation sub-circuit may recurrently (e.g., periodically) drop one or more paces by the electrodes to allow even longer time for a sensing time window in order to detect intrinsic cardiac activity. This may be useful to avoid delivering pacing stimuli that masks intrinsic cardiac events.

In some examples, instead of dropping electrodes, the pacing site activation sub-circuit 325 changes the electrode activation timing. For instance, as the heart rate increases above 80 bpm, the pacing site activation sub-circuit may stop delivery of a pacing stimulus at 60 ms. However, instead of dropping the LV4 electrode from the pacing regimen, the pacing site activation sub-circuit may deliver the pacing stimulus scheduled for 40 ms using both of the LV3 and LV4 electrode. As the heart rate lowers below the 80 bpm threshold or to a hysteretic threshold that is lower than 80 bpm, the pacing site activation sub-circuit 325 re-activates the LV4 electrode separate from the LV3 electrode. Similar to dropping the electrode, changing the electrode time increases the time available for a sensing detection window.

In some embodiments, the pacing site activation sub-circuit 325 reconfigures the electrodes for the pacing stimuli, but continues to use all of the electrodes. As the heart rate increases, the pacing site activation sub-circuit 325 may change the delivery of the pacing stimulation therapy from a first mode in which the pacing stimulation is delivered using a sequence of individual electrodes to a second mode in which the electrical pacing stimulation therapy is delivered using at least two of the individual electrodes electrically coupled together. For instance, below 80 bpm, pacing therapy may be delivered by sequential activation of electrodes LV1 through LV4 with the can electrode 182 in a unipolar pacing mode. Above 80 bpm, the pacing site activation sub-circuit 325 may deliver the pacing stimulus at 35 ms with the LV3 electrode electrically coupled to the LV4 electrode. The pacing site activation sub-circuit 325 may change to separate activation of the LV3 and LV4 electrodes when the heart rate decreases below the threshold or below a hysteretic threshold.

In certain examples, the pacing site activation sub-circuit 325, according to the determined heart rate, changes delivery of the pacing stimulation therapy from a first unipolar pacing mode in which the pacing stimulation is delivered using a can electrode and a sequence of individual electrodes implantable in the left ventricle to a second bipolar pacing mode in which the electrical pacing stimulation therapy is delivered using two LV electrodes. For instance, when the heart rate increases above the 80 bpm threshold, the pacing site activation sub-circuit 325 may change from a unipolar pacing mode, in which pacing pulses are delivered between one or more of the LV electrodes in FIG. 1 and the electrode 182 formed on the housing or electrode 184 formed on the header, to a bipolar mode, such as between LV electrode 165 and ring electrode 160. In another example, when the heart rate increases above 80 bpm, the pacing site activation sub-circuit 325 may change from a unipolar pacing mode to a tripolar mode with electrode L4 as the pacing anode and electrode L2 electrically coupled to electrode L3 as the pacing cathode. The mode change can be useful to increase the time available for a sensing time window and to improve sensing through the combined electrode.

Figure 5:
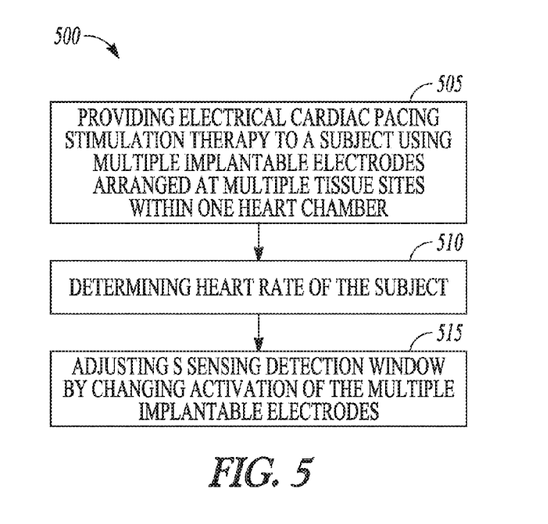
FIG. 5 shows a flow diagram of another example of a method of operating an implantable or otherwise ambulatory medical device.

FIG. 5 shows a flow diagram of another example of a method 500 of operating an implantable or otherwise ambulatory medical device. At 505, electrical cardiac pacing stimulation therapy is provided to a subject using a set of a plurality of implantable electrodes. The implantable electrodes can include multiple implantable electrodes arranged at multiple tissue sites within one heart chamber of the subject. In some examples, pacing stimulation therapy is provided to multiple sites within the left ventricle of the subject.

At 510 heart rate of the subject is determined. The heart rate may be a measured intrinsic heart rate, or the heart rate may be an activity-based pacing rate calculated or otherwise determined by the medical device.

At 515, the sensing time window is adjusted by changing the activation of the electrodes. As described previously, the time available for a sensing time window can be changed by activating and deactivating electrodes, by grouping electrodes together for activation, and by changing between unipolar and bipolar pacing modes. The time available for a sensing time window can also be changed by scaling the delay time between electrode activations according to the heart rate. According to some examples, the pacing delay sub-circuit 335 of FIG. 3 changes the intra-ventricular time delay between delivery of a pacing pulse to an electrode arranged at a first ventricular tissue site and an electrode arranged at a second tissue site of the same ventricle.

Figure 6:
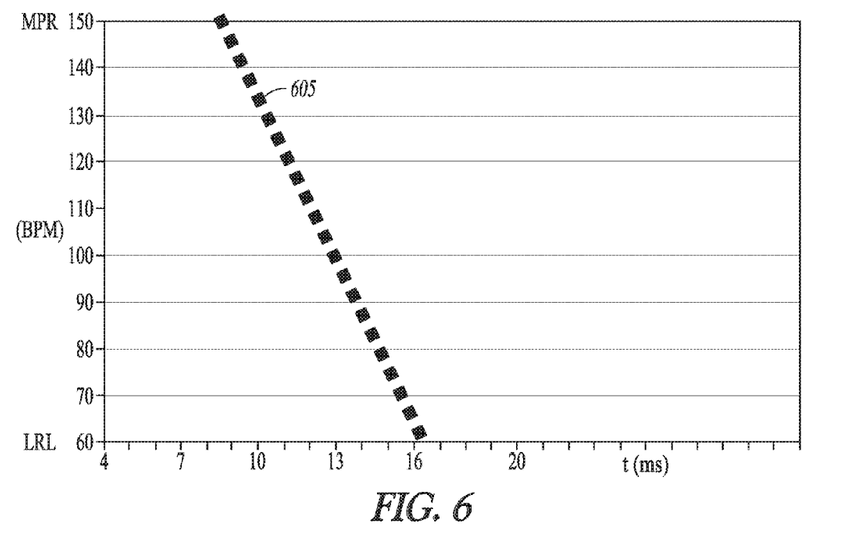
FIG. 6 shows a graph that illustrates an example of a medical device automatically changing electrode activation times according to heart rate.

FIG. 6 shows a graph that illustrates an example of a medical device automatically changing electrode activation times according to heart rate. As an example, the medical device may include two or more of LV electrode 165 (LV1), LV electrode 160 (LV2), LV electrode 164 (LV3), and LV electrode 162 (LV4) in FIG. 1. In some variations, more than four LV electrodes are included with the device. In the example of FIG. 6, the intra-ventricular delay between activation of electrodes arranged in the LV is uniform. The time delay is about 16 ms at the LRL and decreases linearly to about 8 ms at the MPR. Decreasing the intra-ventricular time delay provides more time available for a sensing time window. If there are only two LV electrodes, scaling the time delay may add 8 ms for a sensing time window. If there are six LV electrodes, scaling the time delay may add 40 ms (i.e., 5×8 ms) for a sensing time window at the MPR.

The slope of the line 605 in FIG. 6 is determined by the time delay at the LRL and the time delay at the MPR. The scaling of the time delay may be determined by specifying (e.g., programming) one or more of a time delay at the LRL, a time delay at the MPR, and the slope. In certain examples, multiple slopes are used in the scaling by specifying additional and points of the line or additional slopes.

In some examples, the pacing delay sub-circuit 335 of FIG. 3 changes the inter-ventricular (V-V) time delay according to the determined heart rate. The time delay can be changed between delivery of a pacing pulse to an electrode arranged at a tissue site of a first ventricle and an electrode arranged at a tissue site of the second ventricle (e.g., either RV-LV or LV-RV) to adjust time available for a sensing time window. For instance, if the time delay from delivery of a pacing pulse using RV electrode 140 and can electrode 182 to the delivery of a pacing pulse using LV electrode 165 and can electrode 182 is 50 ms at the LRL and 20 ms at the MPR, scaling the V-V time delay may add 30 ms for a sensing time window at the MPR. This may be in addition to time made available by scaling any intra-ventricular time delays.

In some examples, the pacing delay sub-circuit 335 of FIG. 3 changes the atrial-to-ventricular (A-V) time delay according to the determined heart rate. The time delay between delivery of a pacing pulse to an electrode arranged at a tissue site of an atrium (e.g., right atrium or RA) and an electrode arranged at a tissue site of a ventricle (e.g., one or both of the RV and LV) to adjust time available for a sensing detection window. For instance, if the time delay from the delivery of a pacing pulse using RA electrodes 130 and 125 to the delivery of a pacing pulse using LV electrode 165 and can electrode 182 is 200 ms at the LRL and 100 ms at the MPR, scaling the A-V time delay may add 100 ms for a sensing time window at the MPR. This may be in addition to time made available by scaling one or both of any intra-ventricular time delays and any inter-ventricular time delay.

Figure 7:
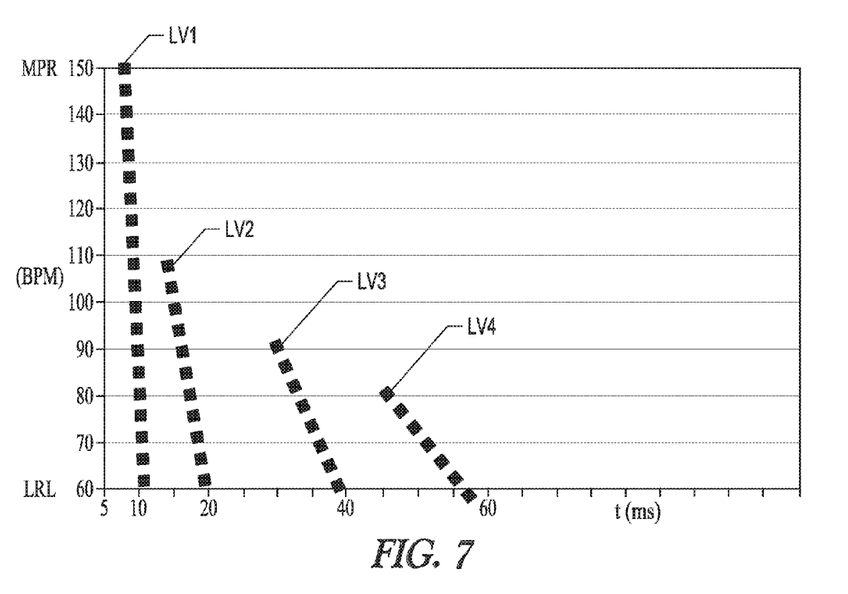
FIG. 7 shows a graph that illustrates an example of a medical device automatically changing electrode activation and times of activation according to heart rate.

According to some embodiments, the time available for a sensing time window can be adjusted by both activating/deactivating electrodes and scaling the inter-electrode pacing delays. FIG. 7 shows a graph that illustrates an example of a medical device automatically changing electrode activation and times of activation according to heart rate. As in the illustrative example of FIG. 4, the electrodes used to deliver the pacing stimuli to the left ventricle may correspond to LV electrode 165 (LV1), LV electrode 160 (LV2), LV electrode 164 (LV3), and LV electrode 162 (LV4) in FIG. 1.

In contrast to the vertical bars in FIG. 4 representing activation times for the electrodes, FIG. 7 shows four sloped lines. The sloped lines intersect the horizontal axis at 10 ms, 20 ms, 40 ms, and 60 ms to represent activation times at the LRL for electrodes LV1, LV2, LV3, and LV4 respectively. For the sloped line for LV4, as the heart rate increases above the LRL, the intra-ventricular time delay between activation of the LV3 electrode and LV4 electrode (LV3-LV4 delay) is decreased from 20 ms. The time delay continues to be decreased until activation of the LV4 electrode is dropped above 80 bpm. Similarly for the sloped line for LV3, as the heart rate increases above the LRL, the time delay between activation of the LV2 electrode and LV3 electrode (LV2-LV3 delay) is decreased from 20 ms. The time delay continues to be decreased until activation of the LV3 electrode is dropped above 95 bpm. For the sloped line for LV2, as the heart rate increases above the LRL, the time delay between activation of the LV1 electrode and LV2 electrode (LV1-LV2 delay) is decreased from 10 ms. The time delay continues to be decreased until activation of the LV3 electrode is dropped above 110 bpm. For the sloped line for LV1, as the heart rate increases above the LRL, the time delay between activation of the RV and LV1 electrode (RV-LV1 delay) is decreased from 10 ms to 7 ms at the MPR. Electrodes may be reactivated at the heart rates at which they were deactivated or hysteresis may be used when reactivating an electrode.

Figure 8:
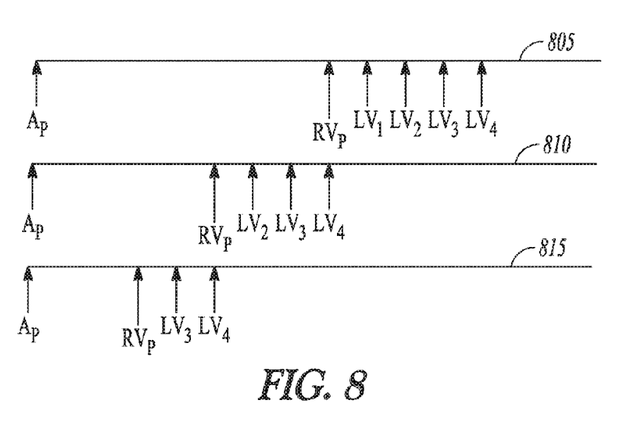
FIG. 8 illustrates another example of a medical device automatically changing electrode activation and times of activation according to heart rate.

FIG. 8 illustrates another example of a medical device automatically changing electrode activation and times of activation according to heart rate. In the top timing diagram 805 of the Figure, an atrial pace stimulus $A_P$ is delivered. The $A_P$ may be delivered according to a device-determined pacing rate. At the expiration of a specified atrial-ventricular (A-V) delay a right ventricle pace stimulus $RV_P$ is delivered. At the expiration of a specified inter-ventricular (V-V) delay a left ventricular pace stimulus (LV1) is delivered. Pacing stimuli are then delivered to pacing electrodes LV2, LV3, LV4 at corresponding pacing sites based on intra-ventricular delays.

In the middle timing diagram 810, the device determined paced heart rate is increased. The A-V delay from $A_P$-$RV_P$ is shown shortened according to heart rate. The middle timing diagram 810 also shows that the LV1 electrode is dropped from the pacing regimen. If the example in FIG. 8 corresponds to the behavior of the device of the example of FIG. 1, pacing therapy may be delivered in a unipolar pacing mode. Pacing therapy may be delivered to the right atrium using lead electrode 130 and can electrode 182. Pacing therapy may be delivered to the right ventricle using lead electrode 135 and can electrode 182. Multi-site pacing therapy may be delivered to the left ventricle using lead electrode 162 (LV1) and the can electrode 182, lead electrode 164 (LV2) and the can electrode 182, lead electrode 160 (LV3) and the can electrode 182, and lead electrode 165(LV4) and the can electrode 182. Electrode LV1 may be dropped first because of its location closest to the device can.

In the bottom timing diagram 815 of FIG. 8, the device determined paced heart rate is increased further. The A-V delay from $A_P$-$RV_P$ is shown shortened by an additional according to heart rate. The bottom timing diagram 815 also shows that the LV2 electrode is dropped from the pacing regimen. Electrode LV3 may be removed if the heart rate increases still further. The electrodes may be restored to the pacing regimen as the heart rate decreases.

Figure 9:
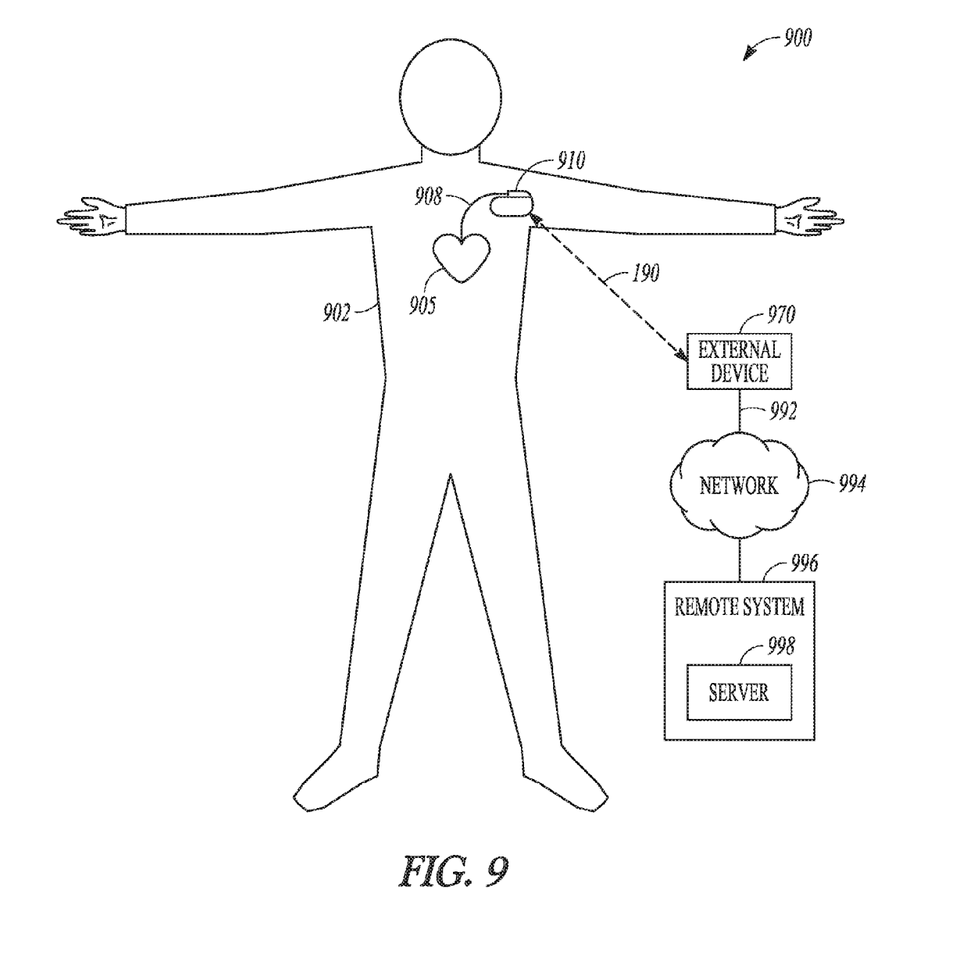
FIG. 9 is an illustration of portions of a system that uses an IMD to provide a therapy to a patient.

FIG. 9 is an illustration of portions of a system 900 that uses a deployed IMD 910 to provide a therapy to a patient 902. The system 900 typically includes an external device 970 that communicates with a remote system 996 via a network 994. The network 994 can be a communication network such as a cellular phone network or a computer network (e.g., the internet). In some examples, the external device 970 includes a repeater and communicated via the network using a link 992 that may be wired or wireless. In some examples, the remote system 996 provides patient management functions and may include one or more servers 998 to perform the functions. In some examples, the remote system 996 provides electrode activation information for use with the methods of multi-site pacing described previously. For instance, the remote system 996 may provide heart rate limits or thresholds at which electrodes can be activated and deactivated. In another example, the remote system 896 may program information into the IMD 910 useful to manage sensing time windows, such as one or both of electrode activation/deactivation and scaling of time delays for electrode activation/deactivation.

ADDITIONAL DESCRIPTION AND EXAMPLES

Example 1 can include subject matter (such as an apparatus) comprising a plurality of electrodes implantable at a plurality of tissue sites of a heart chamber of a subject, a stimulus circuit configured to provide an electrical cardiac pacing stimulation to the plurality of electrodes, a switching circuit configured to select electrodes of the plurality of electrodes for electrical coupling to the stimulus circuit and a control circuit including a heart rate sub-circuit configured to determine heart rate; and including a pacing site activation sub-circuit configured to selectively change which electrodes of the plurality of electrodes are used to provide the electrical cardiac pacing stimulation therapy according to the determined heart rate.

In Example 2, the subject matter of Example 1 can optionally include a plurality of electrodes implantable in a left ventricle of the heart, wherein the apparatus further includes a pacing delay sub-circuit configured to determine a time delay between delivery of a pacing stimulus pulse to a first electrode of the plurality of electrodes implantable in the left ventricle and delivery to a second electrode of the plurality of electrodes implantable in the left ventricle, wherein the pacing site activation sub-circuit is configured to change the electrodes used to provide pacing stimulus pulses to the left ventricle according to the determined heart rate.

In Example 3, the subject matter of one or both of Examples 1 and 2 can optionally include a pacing site activation sub-circuit configured to change, according to the determined heart rate, the delivery of the pacing stimulation therapy from a first mode in which the pacing stimulation is delivered using a sequence of individual electrodes to a second mode in which the electrical pacing stimulation therapy is delivered using at least two of the individual electrodes electrically coupled together.

In Example 4, the subject matter of one or any combination of Examples 1-3 optionally includes a pacing site activation sub-circuit is configured to change, according to the determined heart rate, delivery of the pacing stimulation therapy from a first unipolar pacing mode, in which the pacing stimulation is delivered using a can electrode and a sequence of individual electrodes implantable in the left ventricle, to a second bipolar pacing mode in which the electrical pacing stimulation therapy is delivered using a tip electrode of a lead implantable in a left ventricle and one or more ring electrodes included in the lead.

In Example 5, the subject matter of one or any combination of Examples 1-4 can optionally include a pacing site activation sub-circuit configured to remove an electrode from a set of electrodes used to deliver the pacing stimulation therapy when the determined heart rate increases to a first specified heart rate threshold, and to restore the electrode in the set of electrodes used to deliver the pacing stimulation therapy when the determined heart rate decreases to a second specified heart rate threshold lower than the first heart rate threshold.

In Example 6, the subject matter of one or any combination of Examples 1-5 can optionally include a pacing delay sub-circuit configured to determine a time delay between delivery of a pacing pulse to a first electrode of the plurality of electrodes and at least a second electrode of the plurality of electrodes, and wherein the pacing site activation sub-circuit is configured to remove an electrode corresponding to a latest pacing site activation from a set of electrodes used to deliver the pacing stimulation therapy when the determined heart rate increases to a specified heart rate threshold.

In Example 7, the subject matter of one or any combination of Examples 1-6 can optionally include a physical activity sensing circuit configured to generate an activity signal representative of physical activity of the subject, wherein the heart rate sub-circuit is configured to determine a paced heart rate according to the activity signal and pacing site activation sub-circuit is configured to selectively change electrodes used to provide the electrical cardiac pacing stimulation therapy according to the determined paced heart rate.

In Example 8, the subject matter of one or any combination of Examples 1-7 can optionally include a control circuit that includes a pacing delay sub-circuit configured to change, according to the determined heart rate, an intra-ventricular time delay between delivery of a pacing pulse to an electrode arranged at a first ventricular tissue site and an electrode arranged at a second tissue site of the same ventricle.

In Example 9, the subject matter of one or any combination of Examples 1-8 can optionally include a control circuit that includes a pacing delay sub-circuit configured to change, according to the determined heart rate, an inter-ventricular (V-V) time delay between delivery of a pacing pulse to an electrode arranged at a tissue site of a first ventricle and delivery of a pacing pulse to an electrode arranged at a tissue site of a second ventricle.

In Example 10, the subject matter of one or any combination of Examples 1-9 can optionally include at least one electrode implantable in an atrium of the heart, wherein the pacing delay sub-circuit is configured to change, according to the determined heart rate, an atrial-to-ventricular (A-V) time delay between delivery of a pacing pulse to an electrode arranged at a tissue site of the atrium and delivery of a pacing pulse to an electrode arranged at a tissue site of a ventricle.

In Example 11, the subject matter of one or any combination of Examples 1-10 can optionally include a cardiac signal sensing circuit configured to sense an electrical cardiac activity signal via the electrodes during a specified sensing detection time window of a cardiac cycle; and wherein the control circuit is configured to adjust the specified sensing time window according to the electrode change.

Example 12 can include subject matter (such as a method, a means for performing acts, or a machine-readable medium including instructions that, when performed by the machine, cause the machine to perform acts), or can optionally be combined with the subject matter of one or any combination of Examples 1-11 to include such subject matter, comprising providing electrical cardiac pacing stimulation therapy to a subject using a set of multiple implantable electrodes, determining heart rate of the subject, and selectively changing which electrodes are included in the set of electrodes to provide the electrical cardiac pacing stimulation therapy according to the determined heart rate.

In Example 13, the subject matter of Example 12 can optionally include removing an electrode from a set of electrodes used to deliver the pacing stimulation therapy when the determined heart rate increases to a first specified heart rate threshold, and restoring or replacing the electrode in the set of electrodes used to deliver the pacing stimulation therapy when the determined heart rate decreases to the first specified heart rate threshold.

In Example 14, the subject matter of one or both of Examples 12 and 13 can optionally include providing electrical cardiac pacing stimulation therapy to a left ventricle using a plurality of electrodes implantable in the left ventricle and determining a time delay between delivery of a pacing pulse to a first electrode of the plurality of electrodes implantable in the left ventricle and at least a second electrode of the plurality of electrodes implantable in the left ventricle, and removing an electrode corresponding to a latest pacing site activation from the set of electrodes used to provide electrical pacing stimulation to the left ventricle according to the determined heart rate.

In Example 15, the subject matter of one or any combination of Examples 12-14 can optionally include a plurality of electrodes implantable in a left ventricle of the heart, and changing, according to the determined heart rate, the delivery of the pacing stimulation therapy from a first mode in which the pacing stimulation is delivered using a sequence of individual electrodes to a second mode in which the electrical pacing stimulation therapy is delivered using multiple electrodes electrically coupled together.

In Example 16, the subject matter of one or any combination of Examples 12-15 can optionally include changing, according to the determined heart rate, an intra-ventricular time delay between delivery of a pacing pulse to an electrode arranged at a first ventricular tissue site and an electrode arranged at a second tissue site of the same ventricle.

In Example 17, the subject matter of one or any combination of Examples 12-16 optionally includes changing, according to the determined heart rate, one or both of i) an inter-ventricular (V-V) time delay between delivery of a pacing pulse to an electrode arranged at a tissue site of a first ventricle and an electrode arranged at a tissue site of a second ventricle and ii) an atrial-to-ventricular (A-V) time delay between delivery of a pacing pulse to an electrode arranged at a tissue site of the atrium and an electrode arranged at a tissue site of a ventricle; sensing the electrical cardiac signal during a specified sensing time window of a cardiac cycle; and adjusting the specified sensing time window according to the one or both of the V-V time delay and A-V time delay.

Example 18 can include subject matter (such as an apparatus), or can optionally be combined with the subject matter of one or any combination of Examples 1-17 to include such subject matter, comprising a plurality of electrodes implantable at a plurality of tissue sites of one or both ventricles of a heart of a subject; a stimulus circuit electrically coupled to the plurality of implantable electrodes and configured to provide electrical cardiac pacing stimulation therapy via the electrodes; and a control circuit electrically coupled to the plurality of electrodes and including: a heart rate sub-circuit configured to determine heart rate; and a pacing delay sub-circuit configured to change, according to determined heart rate, an intra-ventricular time delay between delivery of a pacing pulse to an electrode arranged at a first ventricular tissue site and an electrode arranged at a second tissue site of the same ventricle.

In Example 19, the subject matter of Example 18 can optionally include a pacing delay sub-circuit is configured to change, according to the determined heart rate, an inter-ventricular (V-V) time delay between delivery of a pacing pulse to an electrode arranged at a tissue site of a first ventricle and an electrode arranged at a tissue site of a second ventricle.

In Example 20, the subject matter of one or both of Examples 18 and 19 can optionally include at least one electrode implantable in an atrium of the heart, and a sensing circuit electrically coupled to the plurality of implantable electrodes and configured to sense an electrical cardiac activity signal during a specified arrhythmia detection time window, wherein the pacing delay sub-circuit is configured to change, according to the determined heart rate, an atrial-to-ventricular (A-V) time delay between delivery of a pacing pulse to an electrode arranged at a tissue site of the atrium and an electrode arranged at a tissue site of a ventricle, and wherein the control circuit is configured to adjust the specified arrhythmia detection time window according to the change of the A-V time delay.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus for coupling to a plurality of electrodes implantable at a plurality of tissue sites of a heart chamber of a subject, the apparatus comprising:
    a stimulus circuit configured to provide an electrical cardiac pacing stimulation to the plurality of electrodes;
    a switching circuit configured to select electrodes of the plurality of electrodes for electrical coupling to the stimulus circuit; and
    a control circuit including a heart rate sub-circuit configured to determine heart rate; and
    a pacing site activation sub-circuit configured to remove an electrode from the plurality of electrodes to provide the electrical cardiac pacing stimulation therapy when the determined heart rate satisfies a first condition, and to restore the electrode in the plurality of electrodes to provide the electrical cardiac pacing stimulation therapy when the determined heart rate satisfies a different second condition.

2. The apparatus of claim 1, including a plurality of electrodes implantable in a left ventricle of the heart, wherein the apparatus further includes a pacing delay sub-circuit configured to determine a time delay between delivery of a pacing stimulus pulse to a first electrode of the plurality of electrodes implantable in the left ventricle and delivery to a second electrode of the plurality of electrodes implantable in the left ventricle, wherein the pacing site activation sub-circuit is configured to change the electrodes used to provide pacing stimulus pulses to the left ventricle according to the determined heart rate.

3. The apparatus of claim 1, including a plurality of electrodes implantable in a left ventricle of the heart, wherein the pacing site activation sub-circuit is configured to change, according to the determined heart rate, the delivery of the pacing stimulation therapy from a first mode in which the pacing stimulation is delivered using a sequence of individual electrodes to a second mode in which the electrical pacing stimulation therapy is delivered using at least two of the individual electrodes electrically coupled together.

4. The apparatus of claim 1, including a plurality of electrodes implantable in a left ventricle of the heart, wherein the pacing site activation sub-circuit is configured to change, according to the determined heart rate, delivery of the pacing stimulation therapy from a first unipolar pacing mode, in which the pacing stimulation is delivered using a can electrode and a sequence of individual electrodes implantable in the left ventricle, to a second bipolar pacing mode in which the electrical pacing stimulation therapy is delivered using a tip electrode of a lead implantable in a left ventricle and one or more ring electrodes included in the lead.

5. The apparatus of claim 1, wherein the pacing site activation sub-circuit is configured to remove an electrode from a set of electrodes used to deliver the pacing stimulation therapy when the determined heart rate increases to a first specified heart rate threshold, and to restore the electrode in the set of electrodes used to deliver the pacing stimulation therapy when the determined heart rate decreases to a second specified heart rate threshold lower than the first heart rate threshold.

6. The apparatus of claim 1, including a pacing delay sub-circuit configured to determine a time delay between delivery of a pacing pulse to a first electrode of the plurality of electrodes and at least a second electrode of the plurality of electrodes, and wherein the pacing site activation sub-circuit is configured to remove an electrode corresponding to a latest pacing site activation from a set of electrodes used to deliver the pacing stimulation therapy when the determined heart rate increases to a specified heart rate threshold.

7. The apparatus of claim 1, including a physical activity sensing circuit configured to generate an activity signal representative of physical activity of the subject, wherein the heart rate sub-circuit is configured to determine a paced heart rate according to the activity signal and pacing site activation sub-circuit is configured to selectively change electrodes used to provide the electrical cardiac pacing stimulation therapy according to the determined paced heart rate.

8. The apparatus of claim 1, wherein the control circuit includes a pacing delay sub-circuit configured to change, according to the determined heart rate, an intra-ventricular time delay between delivery of a pacing pulse to an electrode arranged at a first ventricular tissue site and an electrode arranged at a second tissue site of the same ventricle.

9. The apparatus of claim 1, wherein the control circuit includes a pacing delay sub-circuit configured to change, according to the determined heart rate, an inter-ventricular (V-V) time delay between delivery of a pacing pulse to an electrode arranged at a tissue site of a first ventricle and delivery of a pacing pulse to an electrode arranged at a tissue site of a second ventricle.

10. The apparatus of claim 1, including at least one electrode implantable in an atrium of the heart, wherein the pacing delay sub-circuit is configured to change, according to the determined heart rate, an atrial-to-ventricular (A-V) time delay between delivery of a pacing pulse to an electrode arranged at a tissue site of the atrium and delivery of a pacing pulse to an electrode arranged at a tissue site of a ventricle.

11. The apparatus of claim 1, including a cardiac signal sensing circuit configured to sense an electrical cardiac activity signal via the electrodes during a specified sensing detection time window of a cardiac cycle; and wherein the control circuit is configured to adjust the specified sensing time window according to the electrode change.

12. A method of operating an implantable or otherwise ambulatory medical device, the method comprising:
providing electrical cardiac pacing stimulation therapy to a subject using a set of multiple implantable electrodes;
determining heart rate of the subject;
removing an electrode from the set of electrodes to provide the electrical cardiac pacing stimulation therapy when the determined heart rate satisfies a first condition; and
restoring the electrode in the set of electrodes to provide the electrical cardiac pacing stimulation therapy when the determined heart rate satisfies a different second condition.

13. The method of claim 12, including removing an electrode from a set of electrodes used to deliver the pacing stimulation therapy when the determined heart rate increases to a first specified heart rate threshold, and restoring the electrode in the set of electrodes used to deliver the pacing stimulation therapy when the determined heart rate decreases to the first specified heart rate threshold.

14. The method of claim 12, wherein providing electrical cardiac pacing stimulation therapy includes providing electrical cardiac pacing stimulation therapy to a left ventricle using a plurality of electrodes implantable in the left ventricle and determining a time delay between delivery of a pacing pulse to a first electrode of the plurality of electrodes implantable in the left ventricle and at least a second electrode of the plurality of electrodes implantable in the left ventricle, and removing, according to the determined heart rate, an electrode corresponding to a latest pacing site activation from the set of electrodes used to provide electrical pacing stimulation to the left ventricle.

15. The method of claim 12, wherein providing electrical cardiac pacing stimulation therapy includes providing electrical cardiac pacing stimulation therapy to a left ventricle using a plurality of electrodes implantable in the left ventricle, and changing, according to the determined heart rate, the delivery of the pacing stimulation therapy from a first mode in which the pacing stimulation is delivered using a sequence of individual electrodes to a second mode in which the electrical pacing stimulation therapy is delivered using multiple electrodes electrically coupled together.

16. The method of claim 12, including changing, according to the determined heart rate, an intra-ventricular time delay between delivery of a pacing pulse to an electrode arranged at a. first ventricular tissue site and an electrode arranged at a second tissue site of the same ventricle.

17. The method of claim 12, including:
changing, according to the determined heart rate, one or both of i) an inter-ventricular (V-V) time delay between delivery of a pacing pulse to an electrode arranged at a tissue site of a first ventricle and an electrode arranged at a tissue site of a second ventricle and ii) an atrial-to-ventricular (A-V) time delay between delivery of a pacing pulse to an electrode arranged at a tissue site of the atrium and an electrode arranged at a tissue site of a ventricle;
sensing the electrical cardiac signal during a specified sensing time window of cardiac cycle; and
adjusting the specified sensing time window according to the one or both of the V-V time delay and A-V time delay.

18. An apparatus for coupling to a plurality of electrodes implantable at a plurality of tissue sites of a heart chamber of a subject, the apparatus comprising:

a stimulus circuit to be electrically coupled to the plurality of implantable electrodes and configured to provide electrical cardiac pacing stimulation therapy via the electrodes; and a control circuit including a heart rate sub-circuit configured to determine heart rate; and a pacing delay sub-circuit configured to change, according to determined heart rate, an intra-ventricular time delay between delivery of a pacing pulse to an electrode arranged at a first ventricular tissue site and an electrode arranged at a second tissue site of the same ventricle.

19. The apparatus of claim 18, wherein the pacing delay sub-circuit is configured to change, according to the determined heart rate, an inter-ventricular (V-V) time delay between delivery of a pacing pulse to an electrode arranged at a tissue site of a first ventricle and an electrode arranged at a tissue site of a second ventricle.

20. The apparatus of claim 18, including a sensing circuit to be electrically coupled to the plurality of implantable electrodes and configured to sense an electrical cardiac activity signal during a specified arrhythmia detection time window, wherein the pacing delay sub-circuit is configured to change, according to the determined heart rate, an atrial-to-ventricular (A-V) time delay between delivery of a pacing pulse to an electrode arranged at a tissue site of the atrium and an electrode arranged at a tissue site of a ventricle, and wherein the control circuit is configured to adjust the specified arrhythmia detection time window according to the change of the A-V time delay.

\* \* \* \* \*